(12) United States Patent
Wu et al.

(10) Patent No.: US 7,635,470 B2
(45) Date of Patent: Dec. 22, 2009

(54) FUNGAL CELL WALL DEGRADING ENZYME

(75) Inventors: Wenping Wu, Beijing (CN); Kirk Matthew Schnorr, Holte (DK)

(73) Assignee: Novozymes A/S, Bagsvaerd (DK)

( * ) Notice: Subject to any disclaimer, the term of this patent is extended or adjusted under 35 U.S.C. 154(b) by 321 days.

(21) Appl. No.: 10/586,026

(22) PCT Filed: Feb. 16, 2006

(86) PCT No.: PCT/DK2005/000099

§ 371 (c)(1),
(2), (4) Date: Jul. 13, 2006

(87) PCT Pub. No.: WO2005/080559

PCT Pub. Date: Sep. 1, 2005

(65) Prior Publication Data

US 2008/0227147 A1    Sep. 18, 2008

Related U.S. Application Data

(60) Provisional application No. 60/550,095, filed on Mar. 4, 2004.

(30) Foreign Application Priority Data

Feb. 25, 2004    (DK) ............................. 2004 00300

(51) Int. Cl.
*A61K 38/46*    (2006.01)
*C12Q 1/34*    (2006.01)
*C12N 9/14*    (2006.01)

(52) U.S. Cl. .................. 424/94.6; 435/18; 435/195; 536/23.2

(58) Field of Classification Search .......... 435/195, 435/200, 203, 207, 18; 424/94.6; 536/23.2
See application file for complete search history.

(56) References Cited

FOREIGN PATENT DOCUMENTS

| EP | 0 425 016 A2 | 5/1991 |
|---|---|---|
| EP | 1 068 871 A1 | 1/2001 |
| GB | 2 331 750 | 6/1999 |
| WO | WO 91/06009 | 5/1991 |

OTHER PUBLICATIONS

Bernard Henrissat, Biochem Journal, vol. 280, pp. 309-316 (1991).
Felch et al, The Journal of Biological Chemistry, vol. 250, Part 10, pp. 3713-3720 (1974).
Seo et al, Journal of BioScience and Bioengineering, vol. 95, No. 3, pp. 313-316 (2003).
Chen et al, Water Research, vol. 34, No. 17, pp. 4229-4233 (2000).
Parkar et al, Journal Ind. Microbial Biotehnology, vol. 30, pp. 553-560 (2003).
Felch et al, Database UNIPROT, Accession No. P00721 (XP-002291508) (1986).
Internet Article on "Cazy —Carbohydrate-Active Enzymes" (XP-002327845) (2005).

*Primary Examiner*—Tekchand Saidha
(74) *Attorney, Agent, or Firm*—Elias Lambiris

(57) ABSTRACT

A novel fungal enzyme having lysozyme activity has been isolated. The invention further relates to a fungal polypeptide having lysozyme activity and belonging to the GH25 family, wherein the enzyme is selected from the group consisting of (a) a polypeptide comprising an amino acid sequence, which has at least 80% identity with amino acids 1 to 233 of SEQ ID NO:2; (b) a polypeptide comprising an amino acid sequence, which has at least 80% identity with the polypeptide encoded by the lysozyme encoding part of the nucleotide sequence inserted into a plasmid present in strain DSM 16084; (c) a polypeptide which is encoded by a nucleotide sequence which hybridizes under high stringency conditions with a polynucleotide probe consisting of the complementary strand of nucleotides 84 to 782 of SEQ ID NO:1; or (d) a fragment of (a), (b) or (c) that has lysozyme activity.

12 Claims, No Drawings

FUNGAL CELL WALL DEGRADING ENZYME

CROSS REFERENCE TO RELATED APPLICATIONS

This application is a 35 U.S.C. 371 national application of PCT/DK2005/000099 filed Feb. 16, 2005, which claims priority or the benefit under 35 U.S.C. 119 of Danish application No. PA 2004 00300 filed Feb. 25, 2004 and U.S. provisional application No. 60/550,095 filed Mar. 4, 2004, the contents of which are fully incorporated herein by reference.

FIELD OF INVENTION

The present invention relates to a fungal enzyme having lysozyme activity, a nucleotide sequence encoding the lysozyme, a nucleic acid construct comprising the nucleotide sequence, methods of producing the lysozyme, as well as uses of the lysozyme.

BACKGROUND OF THE INVENTION

Lysozyme is a O-glycosyl hydrolase produced as a defensive mechanism against bacteria by many organisms. The enzyme causes the hydrolysis of bacterial cell walls by cleaving the glycosidic bonds of peptidoglycan; an important structural molecule in bacteria. After having their cell walls weakened by lysozyme action, bacterial cells lyse resulting from osmotic pressure.

Lysozyme occurs in many organisms such as viruses, plants, insects, birds, reptiles and mammals. In mammals, Lysozyme has been isolated from nasal secretions, saliva, tears, intestines, urine and milk. The enzyme cleaves the glycosidic bond between carbon number 1 of N-acetylmuramic acid and carbon number 4 of N-acetyl-D-glucosamine. In vivo, these two carbohydrates are polymerized to form the cell wall polysaccharide.

Bacteria against which Lysozyme has shown effectiveness include *Clostridium butyricum, Clostridium sporogenes, Clostridium tyrobutyricum, Listeria monocytogenes*.

The lytic action of egg white lysozyme protein is presently being exploited in two markets.

In cheese production, Lysozyme has been found effectively destructive on the vegetative forms of *Clostridia* bacteria and specifically *Clostridium tyrobutyricum*. These bacteria have been found to survive the normal heat treatment of milk used in the production of cheese and later propagate to cause late blowing. Late blowing is the formation of gasses during butyric fermentation occurring in the course of cheese maturation. The effects of the unwanted gas formation can be: faults in texture through the development of irregular-shaped eyes; or obvious undesirable tastes and smells; and finally, the cheese block may completely break apart. With the use of Lysozyme in the milk culture, the production and curing of the cheese may be carried out without concern for butyric fermentation causing late blowing effects. This has led to the wide-spread use of Lysozyme in European cheese production, particularly in the manufacture of medium and long-term ripening cheese. The recommended dosage is 0.2 lbs/1000 gallons milk. The lysozyme must be added after the last heat treatment due to heat instability, and as early as possible before rennet is added due to protease sensitivity.

In pharmacology, Lysozyme's natural function in biological liquids is to attack bacteria foreign to the body. Many bacteria that invade the body through any typical route-eyes, mouth, nose and wounds are challenged with the human immunological system, of which Lysozyme is a critical part. This anti-infectious activity has been exploited in the pharmacological industry by producing pharmaceutical tablets and capsules containing this egg white derived protein. It is also an important component in eye drops, toothpaste and throat lozenges. Potential uses for Lysozyme are varied. Successful results have been determined in cancer research and veterinary applications. As a food preservative, Lysozyme is a natural, organic alternative to many potential carcinogens. Lysozyme's use in baby food applications as well as in animal feed has shown positive results. The potential for this egg white derived enzyme is diverse and research and development on future applications is ongoing.

A GH25 lysozyme has been reported from *Chalaropsis* (Felsch J W, Ingagami T, and Hash J H. (1975) The N,O-Diacetylmuramidase of *Chalaropsis* species; V The complete amino acid sequence. JBC. 250:10 pp 3713-3720).

Hen egg white lysozyme which is the primary product available on the commercial market, does not cleave N,6-O-diacetylmuramidase in e.g. *Streptococcus aureus* cell walls and is thus unable to lyse this important human pathogen among others.

New polypeptides having lysozyme activity is therefore desired.

SUMMARY OF THE INVENTION

The inventors of the present invention have isolated a fungal gene/cDNA encoding an enzyme having lysozyme activity. Such a gene/cDNA encoding the enzyme has to our knowledge not previously been described.

In a first aspect the present invention therefore relates to a fungal polypeptide having lysozyme activity and belonging to the GH25 family.

In a second aspect the present invention relates to a polynucleotide having a nucleotide sequence which encodes for the polypeptide of the invention.

Definitions

Prior to a discussion of the detailed embodiments of the invention, a definition of specific terms related to the main aspects of the invention is provided.

Abbreviations: GlcNAc, N-acetylglucosamine; MurNAc, N-acetylmuramic acid.

Substantially pure polypeptide: In the present context, the term "substantially pure polypeptide" means a polypeptide preparation which contains at the most 10% by weight of other polypeptide material with which it is natively associated (lower percentages of other polypeptide material are preferred, e.g. at the most 8% by weight, at the most 6% by weight, at the most 5% by weight, at the most 4%, at the most 3% by weight, at the most 2% by weight, at the most 1% by weight, and at the most ½% by weight). Thus, it is preferred that the substantially pure polypeptide is at least 92% pure, i.e. that the polypeptide constitutes at least 92% by weight of the total polypeptide material present in the preparation, and higher percentages are preferred such as at least 94% pure, at least 95% pure, at least 96% pure, at least 96% pure, at least 97% pure, at least 98% pure, at least 99% pure, and at the most 99.5% pure. The polypeptides disclosed herein are preferably in a substantially pure form. In particular, it is preferred that the polypeptides disclosed herein are in "essentially pure form", i.e. that the polypeptide preparation is essentially free of other polypeptide material with which it is natively associated. This can be accomplished, for example, by preparing the polypeptide by means of well-known recombinant methods. Herein, the term "substantially pure polypeptide" is synonymous with the terms "isolated polypeptide" and "polypeptide in isolated form".

Lysozyme activity: The term lysozyme activity is defined herein as an O-glycosyl hydrolase, which catalyses the hydrolysis of the glycosidic bond between two or more carbohydrates, or between a carbohydrate and a non-carbohydrate moiety. Lysozymes cleave the glycosidic bond between certain residues in mucopolysaccharides and mucopeptides of bacterial cell walls, resulting in bacteriolysis. Lysozyme belongs to the enzyme class EC 3.2.1.17.

Identity: In the present context, the homology between two amino acid sequences or between two nucleotide sequences is described by the parameter "identity".

For purposes of the present invention, the degree of identity between two amino acid sequences is determined by a Needleman-Wunsch alignment, useful for both protein and DNA alignments. For protein alignments the default scoring matrix used is BLOSUM50, and the penalty for the first residue in a gap is −12, while the penalty for additional residues in a gap is −2. The alignment may be made with the Align software from the FASTA package version v20u6 (W. R. Pearson and D. J. Lipman (1988), "Improved Tools for Biological Sequence Analysis", PNAS 85:2444-2448; and W. R. Pearson (1990) "Rapid and Sensitive Sequence Comparison with FASTP and FASTA", Methods in Enzymology, 183: 63-98).

The degree of identity between two nucleotide sequences may be determined using the same algorithm and software package as described above using the identity matrix as the default scoring matrix. The penalty for the first residue in a gap is −16, while the penalty for additional residues in a gap is −4.

Fragment: When used herein, a "fragment" of SEQ ID NO:2 is a polypeptide retaining its lysozyme activity but having one or more amino acids deleted from the amino and/or carboxyl terminus of this amino acid sequence. Preferably, a fragment contains at the most 208 amino acid residues, e.g., amino acids 20 to 228 of SEQ ID NO:2.

Substantially pure polynucleotide: The term "substantially pure polynucleotide" as used herein refers to a polynucleotide preparation, wherein the polynucleotide has been removed from its natural genetic milieu, and is thus free of other extraneous or unwanted coding sequences and is in a form suitable for use within genetically engineered protein production systems. Thus, a substantially pure polynucleotide contains at the most 10% by weight of other polynucleotide material with which it is natively associated (lower percentages of other polynucleotide material are preferred, e.g. at the most 8% by weight, at the most 6% by weight, at the most 5% by weight, at the most 4% at the most 3% by weight, at the most 2% by weight, at the most 1% by weight, and at the most ½% by weight). A substantially pure polynucleotide may, however, include naturally occurring 5' and 3' untranslated regions, such as promoters and terminators. It is preferred that the substantially pure polynucleotide is at least 92% pure, i.e. that the polynucleotide constitutes at least 92% by weight of the total polynucleotide material present in the preparation, and higher percentages are preferred such as at least 94% pure, at least 95% pure, at least 96% pure, at least 96% pure, at least 97% pure, at least 98% pure, at least 99% pure, and at the most 99.5% pure. The polynucleotides disclosed herein are preferably in a substantially pure form. In particular, it is preferred that the polynucleotides disclosed herein are in "essentially pure form", i.e. that the polynucleotide preparation is essentially free of other polynucleotide material with which it is natively associated. Herein, the term "substantially pure polynucleoude" is synonymous with the terms "isolated polynucleotide" and "polynucleotide in isolated form".

Modification(s): In the context of the present invention the term "modification(s)" is intended to mean any chemical modification of the polypeptide consisting of the amino acid sequence shown as amino acids 1 to 233 of SEQ ID NO:2 as well as genetic manipulation of the DNA encoding that polypeptide. The modification(s) can be replacement(s) of the amino acid side chain(s), substitution(s), deletion(s) and/or insertions(s) in or at the amino acid(s) of interest.

Artificial variant: When used herein, the term "artificial variant" means a polypeptide having lysozyme activity, which has been produced by an organism which is expressing a modified gene as compared to SEQ ID NO:1. The modified gene, from which said variant is produced when expressed in a suitable host, is obtained through human intervention by modification of the nucleotide sequence disclosed in SEQ ID NO:1.

cDNA: The term "cDNA" when used in the present context, is intended to cover a DNA molecule which can be prepared by reverse transcription from a mature, spliced, mRNA molecule derived from a eukaryotic cell. cDNA lacks the intron sequences that are usually present in the corresponding genomic DNA. The initial, primary RNA transcript is a precursor to mRNA and it goes through a series of processing events before appearing as mature spliced mRNA. These events include the removal of intron sequences by a process called splicing. When cDNA is derived from mRNA it therefore lacks intron sequences.

Nucleic acid construct: When used herein, the term "nucleic acid construct" means a nucleic acid molecule, either single- or double-stranded, which is isolated from a naturally occurring gene or which has been modified to contain segments of nucleic acids in a manner that would not otherwise exist in nature. The term nucleic acid construct is synonymous with the term "expression cassette" when the nucleic acid construct contains the control sequences required for expression of a coding sequence of the present invention.

Control sequence: The term "control sequences" is defined herein to include all components, which are necessary or advantageous for the expression of a polypeptide of the present invention. Each control sequence may be native or foreign to the nucleotide sequence encoding the polypeptide. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the nucleotide sequence encoding a polypeptide.

Operably linked: The term "operably linked" is defined herein as a configuration in which a control sequence is appropriately placed at a position relative to the coding sequence of the DNA sequence such that the control sequence directs the expression of a polypeptide.

Coding sequence: When used herein the term "coding sequence" is intended to cover a nucleotide sequence, which directly specifies the amino acid sequence of its protein product. The boundaries of the coding sequence are generally determined by an open reading frame, which usually begins with the ATG start codon. The coding sequence typically include DNA, cDNA, and recombinant nucleotide sequences.

Expression: In the present context, the term "expression" includes any step involved in the production of the polypeptide including, but not limited to, transcription, post-transcriptional modification, translation, post-translational modification, and secretion.

Expression vector: In the present context, the term "expression vector" covers a DNA molecule, linear or circular, that comprises a segment encoding a polypeptide of the invention, and which is operably linked to additional segments that provide for its transcription.

Host cell: The term "host cell", as used herein, includes any cell type which is susceptible to transformation with a nucleic acid construct. In case a bacterial cell is used as the host cell it will not be suitable for expression of the fungal polypeptide of the invention, however, a bacterial host cell may be used for cloning purposes.

The terms "polynucleotide probe", "hybridization" as well as the various stringency conditions are defined in the section entitled "Polypeptides Having Lysozyme Activity".

DETAILED DESCRIPTION OF THE INVENTION

Polypeptides Having Lysozyme Activity

The polypeptide of the invention was isolated from a fungus, more precisely from a *Pycnoporus cinnabarinus* a synonym is *Trametes cinnabarina* in a screening for highly secreted polypeptides and the function of the polypeptide determined.

In a first embodiment, the present invention relates to fungal polypeptide having lysozyme activity and belonging to the GH25 family. The EC 3.2.1.17 enzyme activity classification encompasses enzymes that perform the hydrolysis of the 1,4-beta-linkages between N-acetyl-D-glucosamine and N-acetylmuramic acid in peptidoglycan heteropolymers of the prokaryotes cell wall. An enzyme may have one substrate specificity (for example N-acetylmuramic acid) without the other (N-acetyl-D-glucosamine in this case).

The GH25 family is a classification of enzymes according to the Henrissat glycosyl hydrolase family classification (Henrissat B., A classification of glycosyl hydrolases based on amino-acid sequence similarities. Biochem. J. 280:309-316(1991); Henrissat B., Bairoch A. New families in the classification of glycosyl hydrolases based on amino-acid sequence similarities. Biochem. J. 293:781-788(1993); Henrissat B., Bairoch A. Updating the sequence-based classification of glycosyl hydrolases. Biochem. J. 316:695-696(1996); Davies G., Henrissat B. Structures and mechanisms of glycosyl hydrolases. Structure 3:853-859(1995)).

Besides GH25, other enzyme hydrolase families with lysozyme (EC 3.2.1.17) activity are GH22, GH23 and GH24. Family GH22, or lysozyme C includes hen egg white lysozyme and the stomach lysozymes of ruminants. This family is the most extensively studied of the four families. GH23 commonly known as lysozyme G is represented by Goose and a number of less well studied phage and bacterial sequences from genome sequencing projects. GH24 includes notably phage T4 and other phage and bacterial lysozymes. Research by Seo et al. 2003 (Seo H J; Kitaoka M; Ohmiya K; Hayashi K., (2003) Substrate specificity of the N,6-O-diacetylmuramidase from *Streptomyces globisporus*. Journal of Bioscience and Bioengineering, Vol. 95 (3) pp. 313-316) have shown that, at least in the case of *Streptomyces globisporus* GH25 enzyme, a different activity spectra was observed compared to hen egg white lysozyme GH22. The *Streptomyces* enzyme possesses both N-acetylmuramidase and N,6-O-diacetylmuramidase activity. This allowed the *Streptomyces globisporus* enzyme to degrade *Staphylococcus aureus* cell walls, which are highly acetylated. This activity may be extrapolatable to other lysozyme enzymes in this family such as the lysozyme GH25 of the invention.

In a further embodiment the present invention relates to polypeptides where the polypeptides comprises, preferably consists of, an amino acid sequence which has a degree of identity to amino acids 1 to 233 of SEQ ID NO:2 of at least 65%, preferably at least 70%, e.g. at least 75%, more preferably at least 80%, such as at least 85%, even more preferably at least 90%, most preferably at least 95%, e.g. at least 96%, such as at least 97%, and even most preferably at least 98%, such as at least 99% (hereinafter "homologous polypeptides"). In an interesting embodiment, the amino acid sequence differs by at the most ten amino acids (e.g. by ten amino acids), in particular by at the most five amino acids (e.g. by five amino acids), such as by at the most four amino acids (e.g. by four amino acids), e.g. by at the most three amino acids (e.g. by three amino acids) from amino acids 1 to 233 of SEQ ID NO:2. In a particular interesting embodiment, the amino acid sequence differs by at the most two amino acids (e.g. by two amino acids), such as by one amino acid from amino acids 1 to 233 of SEQ ID NO:2.

Preferably, the polypeptides of the present invention comprise the amino acid sequence of SEQ ID NO:2; an allelic variant thereof; or a fragment thereof that has lysozyme activity. In another preferred embodiment, the polypeptide of the present invention comprises amino acids 1 to 233 of SEQ ID NO:2. In a further preferred embodiment, the polypeptide consists of amino acids 1 to 233 of SEQ ID NO:2.

Polypeptides of the invention may be a wild type lysozyme identified and isolated from a natural source. Such wild-type polypeptides may be specifically identified e.g. by a bioinformatics approach, which is one method that can be used to identify lysozyme candidates. Briefly GH25 lysozyme candidates can be directly identified in a genome or cDNA sequencing project by using a known lysozyme of family GH25 as the search sequence. Another method is to compare all of the unique DNA fragments (contigs) a standard homology search program such as WU-BlastX (2.0a19MP_WashU).

Furthermore, the polypeptide of the invention may be prepared by the DNA shuffling technique, such as described in J. E. Ness et al. *Nature Biotechnology* 17, 893-896 (1999). Moreover, the polypeptide of the invention may be an artificial variant which comprises, preferably consists of, an amino acid sequence that has at least one substitution, deletion and/or insertion of an amino acid as compared to amino acids 1 to 233 of SEQ ID NO:2. Such artificial variants may be constructed by standard techniques known in the art, such as by site-directed/random mutagenesis of the polypeptide comprising the amino acid sequence shown as amino acids 1 to 233 of SEQ ID NO:2. In one embodiment of the invention, amino acid changes (in the artificial variant as well as in wild-type polypeptides) are of a minor nature, that is conservative amino acid substitutions that do not significantly affect the folding and/or activity of the protein; small deletions, typically of one to about 30 amino acids; small amino- or carboxyl-terminal extensions, such as an amino-terminal methionine residue; a small linker peptide of up to about 20-25 residues; or a small extension that facilitates purification by changing net charge or another function, such as a poly-histidine tract, an antigenic epitope or a binding domain.

Examples of conservative substitutions are within the group of basic amino acids (arginine, lysine and histidine), acidic amino acids (glutamic acid and aspartic acid), polar amino acids (glutamine and asparagine), hydrophobic amino acids (leucine, isoleucine, valine and methionine), aromatic amino acids (phenylalanine, tryptophan and tyrosine), and small amino acids (glycine, alanine, serine and threonine). Amino acid substitutions which do not generally alter the specific activity are known in the art and are described, for example, by H. Neurath and R. L. Hill, 1979, *In, The Proteins*, Academic Press, New York. The most commonly occurring exchanges are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly as well as these in reverse.

In an interesting embodiment of the invention, the amino acid changes are of such a nature that the physico-chemical properties of the polypeptides are altered. For example, amino acid changes may be performed, which improve the thermal stability of the polypeptide, which alter the substrate specificity, which changes the pH optimum, and the like.

Preferably, the number of such substitutions, deletions and/or insertions as compared to amino acids 1 to 233 of SEQ ID NO:2 is at the most 10, such as at the most 9, e.g. at the most 8, more preferably at the most 7, e.g. at the most 6, such as at the most 5, most preferably at the most 4, e.g. at the most 3, such as at the most 2, in particular at the most 1.

In a another embodiment, the present invention relates to polypeptides having lysozyme activity which are encoded by nucleotide sequences which hybridize under very low stringency conditions, preferably under low stringency conditions, more preferably under medium stringency conditions, more preferably under medium-high stringency conditions, even more preferably under high stringency conditions, and most preferably under very high stringency conditions with a polynucleotide probe consisting of the complementary strand of nucleotides 84 to 782 of SEQ ID NO:1 (J. Sambrook, E. F. Fritsch, and T. Maniatis, 1989, *Molecular Cloning, A Laboratory Manual,* 2d edition, Cold Spring Harbor, New York).

The nucleotide sequence of SEQ ID NO:1 or a subsequence thereof, as well as the amino acid sequence of SEQ ID NO:2 or a fragment thereof, may be used to design a polynucleotide probe to identify, and clone DNA encoding polypeptides having lysozyme activity from strains of different genera or species according to methods well known in the art. In particular, such probes can be used for hybridization with the genomic or cDNA of the genus or species of interest, following standard Southern blotting procedures, in order to identify and isolate the corresponding gene therein. Such probes can be considerably shorter than the entire sequence, but should be at least 15, preferably at least 25, more preferably at least 35 nucleotides in length, such as at least 70 nucleotides in length. It is, however, preferred that the polynucleotide probe is at least 100 nucleotides in length. For example, the polynucleotide probe may be at least 200 nucleotides in length, at least 300 nucleotides in length, at least 400 nucleotides in length or at least 500 nucleotides in length. Even longer probes may be used, e.g., polynucleotide probes which are at least 600 nucleotides in length, at least 700 nucleotides in length, at least 800 nucleotides in length, or at least 900 nucleotides in length. Both DNA and RNA probes can be used. The probes are typically labeled for detecting the corresponding gene (for example, with $^{32}P$, $^{3}H$, $^{35}S$, biotin, or avidin).

Thus, a genomic DNA or cDNA library prepared from such other organisms may be screened for DNA which hybridizes with the probes described above and which encodes a polypeptide having lysozyme activity. Genomic or other DNA from such other organisms may be separated by agarose or polyacrylamide gel electrophoresis, or other separation techniques. DNA from the libraries or the separated DNA may be transferred to, and immobilized on nitrocellulose or other suitable carrier materials. In order to identify a clone or DNA which is homologous with SEQ ID NO:1 the carrier material with the immobilized DNA is used in a Southern blot.

For purposes of the present invention, hybridization indicates that the nucleotide sequence hybridizes to a labeled polynucleotide probe which hybridizes to the nucleotide sequence shown in SEQ ID NO:1 under very low to very high stringency conditions. Molecules to which the polynucleotide probe hybridizes under these conditions may be detected using X-ray film or by any other method known in the art. Whenever the term "polynucleotide probe" is used in the present context, it is to be understood that such a probe contains at least 15 nucleotides.

In an interesting embodiment, the polynucleotide probe is the complementary strand of nucleotides 84 to 782 of SEQ ID NO:1.

In another interesting embodiment, the polynucleotide probe is the complementary strand of the nucleotide sequence which encodes the polypeptide of SEQ ID NO:2. In a further interesting embodiment, the polynucleotide probe is the complementary strand of SEQ ID NO:1. In a still further interesting embodiment, the polynucleotide probe is the complementary strand of the mature polypeptide coding region of SEQ ID NO:1.

For long probes of at least 100 nucleotides in length, very low to very high stringency conditions are defined as prehybridization and hybridization at 42° C. in 5× SSPE, 1.0% SDS, 5× Denhardt's solution, 100 µg/ml sheared and denatured salmon sperm DNA, following standard Southern blotting procedures. Preferably, the long probes of at least 100 nucleotides do not contain more than 1000 nucleotides. For long probes of at least 100 nucleotides in length, the carrier material is finally washed three times each for 15 minutes using 2×SSC, 0.1% SDS at 42° C. (very low stringency), preferably washed three times each for 15 minutes using 0.5×SSC, 0.1% SDS at 42° C. (low stringency), more preferably washed three times each for 15 minutes using 0.2×SSC, 0.1% SDS at 42° C. (medium stringency), even more preferably washed three times each for 15 minutes using 0.2×SSC, 0.1% SDS at 55° C. (medium-high stringency), most preferably washed three times each for 15 minutes using 0.1×SSC, 0.1% SDS at 60° C. (high stringency), in particular washed three times each for 15 minutes using 0.1×SSC, 0.1% SDS at 68° C. (very high stringency).

Although not particularly preferred, it is contemplated that shorter probes, e.g. probes which are from about 15 to 99 nucleotides in length, such as from about 15 to about 70 nucleotides in length, may be also be used. For such short probes, stringency conditions are defined as prehybridization, hybridization, and washing post-hybridization at 5° C. to 10° C. below the calculated $T_m$ using the calculation according to Bolton and McCarthy (1962, *Proceedings of the National Academy of Sciences USA* 48:1390) in 0.9 M NaCl, 0.09 M Tris-HCl pH 7.6, 6 mM EDTA, 0.5% NP-40, 1× Denhardt's solution, 1 mM sodium pyrophosphate, 1 mM sodium monobasic phosphate, 0.1 mM ATP, and 0.2 mg of yeast RNA per ml following standard Southern blotting procedures.

For short probes which are about 15 nucleotides to 99 nucleotides in length, the carrier material is washed once in 6×SCC plus 0.1% SDS for 15 minutes and twice each for 15 minutes using 6×SSC at 5° C. to 10° C. below the calculated $T_m$.

Lysozyme Activity

Several assays have been described for the determination of lysozyme activity. One assay described in J. Biochem. (H. Maeda, 1980, vol. 88 (4): 1185-1191) is based on either fluorescence polarization or fluorescence intensity using fluorescein-labeled peptidoglycan as a substrate, which was obtained from *Micrococcus lysodeikticus*.

Another assay is based on the clearance of a *Micrococcus luteus* suspension caused by lysozyme and monitored at 450 nm and compared to a lysozyme standard of known activity. This assay was developed at the FIP Center for Standards, International Commission on Pharmaceutical Enzymes, Harelbekestaat 72, B-9000 gent, Belgium. This assay requires the use of lyophilized, viable *M. luteus* ATCC 4698 cells. This substrate is available from the Center for Standards as well as a detailed protocol.

Another assay, EnzChek® Lysozyme Assay Kit (E-22013), is available from Molecular Probes, and is based on a measure of lysozyme activity on *Micrococcus lysodeikticus* cell walls that are labeled with fluorescein.

Sources for Polypeptides Having Lysozyme Activity

A polypeptide of the present invention is a fungal polypeptide. "Fungi" as used herein includes the phyla Ascomycota, Basidiomycota, Chytridiomycota, and Zygomycota (as defined by Hawksworth et al., *In, Ainsworth and Bisby's Dictionary of The Fungi*, 8th edition, 1995, CAB International, University Press, Cambridge, UK) as well as the Oomycota (as cited in Hawksworth et al., 1995, supra, page 171) and all mitosporic fungi (Hawksworth et al., 1995, supra).

In a particular embodiment, the fungal polypeptide is a yeast polypeptide. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in *Biology and Activities of Yeast* (Skinner, F. A., Passmore, S. M., and Davenport, R. R., eds, *Soc. App. Bacteriol. Symposium Series* No. 9, 1980).

The yeast polypeptide is in a particular embodiment a *Candida, Kluyveromyces, Pichia, Saccharomyces, Schizosaccharomyces,* or *Yarrowia* polypeptide. In an interesting embodiment, the polypeptide is a *Saccharomyces carlsbergensis, Saccharomyces cerevisiae, Saccharomyces diastaticus, Saccharomyces douglasii, Saccharomyces kluyveri, Saccharomyces norbensis* or *Saccharomyces oviformis* polypeptide.

In another particular embodiment the fungal polypeptide of the invention is a filamentous fungal polypeptide such as an *Acremonium, Aspergillus, Aureobasidium, Cryptococcus, Filibasidium, Fusarium, Humicola, Magnaporthe, Mucor, Myceliophthora, Neocallimastix, Neurospora, Paecilomyces, Penicillium, Piromyces, Schizophyllum, Talaromyces, Thermoascus, Thielavia, Tolypocladium,* or *Trichoderma* polypeptide.

In another interesting embodiment, the polypeptide is an *Aspergillus aculeatus, Aspergillus awamori, Aspergillus foetidus, Aspergillus fumigatus, Aspergillus japonicus, Aspergillus nidulans, Aspergillus niger, Aspergillus oryzae, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola insolens, Humicola lanuginosa, Mucor miehei, Myceliophthora thermophila, Neurospora crassa, Penicillium purpurogenum, Thielavia terrestris, Trichoderma harzianum, Trichoderma koningii, Trichoderma longibrachiatum, Trichoderma reesei,* or *Trichoderma viride* polypeptide.

It will be understood that for the aforementioned species, the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen und Zellkulturen GmbH (DSM), Centraalbureau Voor Schimmelcultures (CBS), and Agricultural Research Service Patent Culture Collection, Northern Regional Research Center (NRRL).

Furthermore, such polypeptides may be identified and obtained from other sources including microorganisms isolated from nature (e.g., soil, composts, water, etc.) using the above-mentioned probes. Techniques for isolating microorganisms from natural habitats are well known in the art. The nucleotide sequence may then be derived by similarly screening a genomic or cDNA library of another microorganism. Once a nucleotide sequence encoding a polypeptide has been detected with the probe(s), the sequence may be isolated or cloned by utilizing techniques which are known to those of ordinary skill in the art (see, e.g., Sambrook et al., 1989, supra).

Polypeptides encoded by nucleotide sequences of the present invention also include fused polypeptides or cleavable fusion polypeptides in which another polypeptide is fused at the N-terminus or the C-terminus of the polypeptide or fragment thereof. A fused polypeptide is produced by fusing a nucleotide sequence (or a portion thereof) encoding another polypeptide to a nucleotide sequence (or a portion thereof) of the present invention. Techniques for producing fusion polypeptides are known in the art, and include ligating the coding sequences encoding the polypeptides so that they are in frame and that expression of the fused polypeptide is under control of the same promoter(s) and terminator.

Polynucleotides and Nucleotide Sequences

The present invention also relates to polynucleotides having a nucleotide sequence which encodes for a polypeptide of the invention. In particular, the present invention relates to polynucleotides consisting of a nucleotide sequence which encodes for a polypeptide of the invention. In a particular embodiment, the nucleotide sequence is set forth in SEQ ID NO:1. In a more particular embodiment, the nucleotide sequence 139-724 is the mature polypeptide coding region of SEQ ID NO:1.

The present invention also encompasses polynucleotides having, preferably consisting of, nucleotide sequences which encode a polypeptide consisting of the amino acid sequence of SEQ ID NO:2 or the mature polypeptide thereof, which differ from SEQ ID NO:1 by virtue of the degeneracy of the genetic code.

The present invention also relates to polynucleotides having, preferably consisting of, a subsequence of SEQ ID NO:1 which encode fragments of SEQ ID NO:2 that have lysozyme activity. A subsequence of SEQ ID NO:1 is a nucleotide sequence encompassed by SEQ ID NO:1 except that one or more nucleotides from the 5' and/or 3' end have been deleted.

The present invention also relates to polynucleotides having, preferably consisting of, a modified nucleotide sequence which comprises at least one modification in the mature polypeptide coding sequence of SEQ ID NO:1, and where the modified nucleotide sequence encodes a polypeptide which consists of amino acids 19 to 233 of SEQ ID NO:2.

The techniques used to isolate or clone a nucleotide sequence encoding a polypeptide are known in the art and include isolation from genomic DNA, preparation from cDNA, or a combination thereof. The cloning of the nucleotide sequences of the present invention from such genomic DNA can be effected, e.g., by using the well known polymerase chain reaction (PCR) or antibody screening of expression libraries to detect cloned DNA fragments with shared structural features. See, e.g., Innis et al., 1990, *PCR: A Guide to Methods and Application*, Academic Press, New York. Other amplification procedures such as ligase chain reaction (LCR), ligated activated transcription (LAT) and nucleotide sequence-based amplification (NASBA) may be used. The nucleotide sequence may be cloned from a strain of *Aspergillus*, or another or related organism and thus, for example, may be an allelic or species variant of the polypeptide encoding region of the nucleotide sequence.

The nucleotide sequence may be obtained by standard cloning procedures used in genetic engineering to relocate the nucleotide sequence from its natural location to a different site where it will be reproduced. The cloning procedures may involve excision and isolation of a desired fragment comprising the nucleotide sequence encoding the polypeptide, insertion of the fragment into a vector molecule, and incorporation of the recombinant vector into a host cell where multiple copies or clones of the nucleotide sequence will be replicated. The nucleotide sequence may be of genomic, cDNA, RNA, semisynthetic, synthetic origin, or any combinations thereof.

The present invention also relates to a polynucleotide having, preferably consisting of, a nucleotide sequence which has at least 65% identity with nucleotides 84 to 782 of SEQ ID NO:1. Preferably, the nucleotide sequence has at least 70% identity, e.g. at least 80% identity, such as at least 90% identity, more preferably at least 95% identity, such as at least 96% identity, e.g. at least 97% identity, even more preferably at least 98% identity, such as at least 99% with nucleotides 84 to 782 of SEQ ID NO:1. Particularly, the nucleotide sequence encodes a polypeptide having lysozyme activity. The degree of identity between two nucleotide sequences is determined as described previously (see the section entitled "Definitions").

Modification of a nucleotide sequence encoding a polypeptide of the present invention may be necessary for the synthesis of a polypeptide, which comprises an amino acid sequence that has at least one substitution, deletion and/or insertion as compared to amino acids 1 to 233 of SEQ ID NO:2. These artificial variants may differ in some engineered way from the polypeptide isolated from its native source, e.g., variants that differ in specific activity, thermostability, pH optimum, or the like.

It will be apparent to those skilled in the art that such modifications can be made outside the regions critical to the function of the molecule and still result in an active polypeptide. Amino acid residues essential to the activity of the polypeptide encoded by the nucleotide sequence of the invention, and therefore preferably not subject to modification, such as substitution, may be identified according to procedures known in the art, such as site-directed mutagenesis or alanine-scanning mutagenesis (see, e.g., Cunningham and Wells, 1989, *Science* 244: 1081-1085). In the latter technique, mutations are introduced at every positively charged residue in the molecule, and the resultant mutant molecules are tested for lysozyme activity (as described in the examples) to identify amino acid residues that are critical to the activity of the molecule. Sites of substrate-enzyme interaction can also be determined by analysis of the three-dimensional structure as determined by such techniques as nuclear magnetic resonance analysis, crystallography or photoaffinity labelling (see, e.g., de Vos et al., 1992, *Science* 255: 306-312; Smith et al., 1992, *Journal of Molecular Biology* 224: 899-904; Wlodaver et al., 1992, *FEBS Letters* 309: 59-64).

Moreover, a nucleotide sequence encoding a polypeptide of the present invention may be modified by introduction of nucleotide substitutions which do not give rise to another amino acid sequence of the polypeptide encoded by the nucleotide sequence, but which correspond to the codon usage of the host organism intended for production of the enzyme.

The introduction of a mutation into the nucleotide sequence to exchange one nucleotide for another nucleotide may be accomplished by site-directed mutagenesis using any of the methods known in the art. Particularly useful is the procedure, which utilizes a supercoiled, double stranded DNA vector with an insert of interest and two synthetic primers containing the desired mutation. The oligonucleotide primers, each complementary to opposite strands of the vector, extend during temperature cycling by means of Pfu DNA polymerase. On incorporation of the primers, a mutated plasmid containing staggered nicks is generated. Following temperature cycling, the product is treated with Dpnl which is specific for methylated and hemimethylated DNA to digest the parental DNA template and to select for mutation-containing synthesized DNA. Other procedures known in the art may also be used. For a general description of nucleotide substitution, see, e.g., Ford et al., 1991, *Protein Expression and Purification* 2: 95-107.

The present invention also relates to a polynucleotide having, preferably consisting of, a nucleotide sequence which encodes a polypeptide having lysozyme activity, and which hybridizes under very low stringency conditions, preferably under low stringency conditions, more preferably under medium stringency conditions, more preferably under medium-high stringency conditions, even more preferably under high stringency conditions, and most preferably under very high stringency conditions with a polynucleotide probe consisting of the complementary strand of nucleotides 84 to 782 of SEQ ID NO:1.

As will be understood, details and particulars concerning hybridization of the nucleotide sequences will be the same or analogous to the hybridization aspects discussed in the section entitled "Polypeptides having Lysozyme Activity" herein.

Nucleic Acid Constructs

The present invention also relates to nucleic acid constructs comprising a nucleotide sequence of the present invention operably linked to one or more control sequences that direct the expression of the coding sequence in a suitable host cell under conditions compatible with the control sequences.

A nucleotide sequence encoding a polypeptide of the present invention may be manipulated in a variety of ways to provide for expression of the polypeptide. Manipulation of the nucleotide sequence prior to its insertion into a vector may be desirable or necessary depending on the expression vector. The techniques for modifying nucleotide sequences utilizing recombinant DNA methods are well known in the art.

The control sequence may be an appropriate promoter sequence, a nucleotide sequence which is recognized by a host cell for expression of the nucleotide sequence. The promoter sequence contains transcriptional control sequences, which mediate the expression of the polypeptide. The promoter may be any nucleotide sequence which shows transcriptional activity in the host cell of choice including mutant, truncated, and hybrid promoters, and may be obtained from genes encoding extracellular or intracellular polypeptides either homologous or heterologous to the host cell.

Examples of suitable promoters for directing the transcription of the nucleic acid constructs of the present invention in a filamentous fungal host cell are promoters obtained from the genes for *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase, and *Fusarium oxysporum* trypsin-like protease (WO 96/00787), as well as the NA2-tpi promoter (a hybrid of the promoters from the genes for *Aspergillus niger* neutral alpha-amylase and *Aspergillus oryzae* triose phosphate isomerase), and mutant, truncated, and hybrid promoters thereof.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH2/GAP), and *Saccharomyces cerevisiae* 3-phosphoglycerate kinase. Other useful promoters for yeast host cells are described by Romanos et al., 1992, *Yeast* 8: 423-488.

The control sequence may also be a suitable transcription terminator sequence, a sequence recognized by a host cell to terminate transcription. The terminator sequence is operably linked to the 3' terminus of the nucleotide sequence encoding the polypeptide. Any terminator which is functional in the host cell of choice may be used in the present invention.

Preferred terminators for filamentous fungal host cells are obtained from the genes for *Aspergillus oryzae* TAKA amylase, *Aspergillus niger* glucoamylase, *Aspergillus nidulans* anthranilate synthase, *Aspergillus niger* alpha-glucosidase, and *Fusarium oxysporum* trypsin-like protease.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be a suitable leader sequence, a non-translated region of an mRNA which is important for translation by the host cell. The leader sequence is operably linked to the 5' terminus of the nucleotide sequence encoding the polypeptide. Any leader sequence that is functional in the host cell of choice may be used in the present invention.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3' terminus of the nucleotide sequence and which, when transcribed, is recognized by the host cell as a signal to add polyadenosine residues to transcribed mRNA. Any polyadenylation sequence which is functional in the host cell of choice may be used in the present invention.

Preferred polyadenylation sequences for filamentous fungal host cells are obtained from the genes for *Aspergillus oryzae* TAKA amylase, *Aspergillus niger* glucoamylase, *Aspergillus nidulans* anthranilate synthase, *Fusarium oxysporum* trypsin-like protease, and *Aspergillus niger* alpha-glucosidase.

Useful polyadenylation sequences for yeast host cells are described by Guo and Sherman, 1995, *Molecular Cellular Biology* 15: 5983-5990.

The control sequence may also be a signal peptide coding region that codes for an amino acid sequence linked to the amino terminus of a polypeptide and directs the encoded polypeptide into the cell's secretory pathway. The 5' end of the coding sequence of the nucleotide sequence may inherently contain a signal peptide coding region naturally linked in translation reading frame with the segment of the coding region which encodes the secreted polypeptide. Alternatively, the 5' end of the coding sequence may contain a signal peptide coding region which is foreign to the coding sequence. The foreign signal peptide coding region may be required where the coding sequence does not naturally contain a signal peptide coding region. Alternatively, the foreign signal peptide coding region may simply replace the natural signal peptide coding region in order to enhance secretion of the polypeptide. However, any signal peptide coding region which directs the expressed polypeptide into the secretory pathway of a host cell of choice may be used in the present invention.

The signal peptide coding region is nucleotides 84 to 138 of SEQ ID NO:1 which encode amino acids 1 to 18 of SEQ ID NO:2.

Effective signal peptide coding regions for filamentous fungal host cells are the signal peptide coding regions obtained from the genes for *Aspergillus oryzae* TAKA amylase, *Aspergillus niger* neutral amylase, *Aspergillus niger* glucoamylase, *Rhizomucor miehei* aspartic proteinase, *Humicola insolens* cellulase, and *Humicola lanuginosa* lipase.

Useful signal peptides for yeast host cells are obtained from the genes for *Saccharomyces cerevisiae* alpha-factor and *Saccharomyces cerevisiae* invertase. Other useful signal peptide coding regions are described by Romanos et al., 1992, supra.

The control sequence may also be a propeptide coding region that codes for an amino acid sequence positioned at the amino terminus of a polypeptide. The resultant polypeptide is known as a proenzyme or propolypeptide (or a zymogen in some cases). A propolypeptide is generally inactive and can be converted to a mature active polypeptide by catalytic or autocatalytic cleavage of the propeptide from the propolypeptide.

Where both signal peptide and propeptide regions are present at the amino terminus of a polypeptide, the propeptide region is positioned next to the amino terminus of a polypeptide and the signal peptide region is positioned next to the amino terminus of the propeptide region.

It may also be desirable to add regulatory sequences which allow the regulation of the expression of the polypeptide relative to the growth of the host cell. Examples of regulatory systems are those which cause the expression of the gene to be turned on or off in response to a chemical or physical stimulus, including the presence of a regulatory compound. Regulatory systems in yeast include the ADH2 system or GAL1 system, which may be used. In filamentous fungi, the TAKA alpha-amylase promoter, *Aspergillus niger* glucoamylase promoter, and *Aspergillus oryzae* glucoamylase promoter may be used as regulatory sequences. Other examples of regulatory sequences are those which allow for gene amplification. In eukaryotic systems, these include the dihydrofolate reductase gene which is amplified in the presence of methotrexate, and the metallothionein genes which are amplified with heavy metals. In these cases, the nucleotide sequence encoding the polypeptide would be operably linked with the regulatory sequence.

Expression Vectors

The present invention also relates to recombinant expression vectors comprising the nucleic acid construct of the invention. The various nucleotide and control sequences described above may be joined together to produce a recombinant expression vector which may include one or more convenient restriction sites to allow for insertion or substitution of the nucleotide sequence encoding the polypeptide at such sites. Alternatively, the nucleotide sequence of the present invention may be expressed by inserting the nucleotide sequence or a nucleic acid construct comprising the sequence into an appropriate vector for expression. In creating the expression vector, the coding sequence is located in the vector so that the coding sequence is operably linked with the appropriate control sequences for expression.

The recombinant expression vector may be any vector (e.g., a plasmid or virus) which can be conveniently subjected to recombinant DNA procedures and can bring about the expression of the nucleotide sequence. The choice of the vector will typically depend on the compatibility of the vector with the host cell into which the vector is to be introduced. The vectors may be linear or closed circular plasmids.

The vector may be an autonomously replicating vector, i.e., a vector which exists as an extrachromosomal entity, the replication of which is independent of chromosomal replication, e.g., a plasmid, an extrachromosomal element, a minichromosome, or an artificial chromosome.

The vector may contain any means for assuring self-replication. Alternatively, the vector may be one which, when introduced into the host cell, is integrated into the genome and replicated together with the chromosome(s) into which it has been integrated. Furthermore, a single vector or plasmid or two or more vectors or plasmids which together contain the total DNA to be introduced into the genome of the host cell, or a transposon may be used.

The vectors of the present invention preferably contain one or more selectable markers which permit easy selection of transformed cells. A selectable marker is a gene the product of which provides for biocide or viral resistance, resistance to heavy metals, prototrophy to auxotrophs, and the like.

Suitable markers for yeast host cells are ADE2, HIS3, LEU2, LYS2, MET3, TRP1, and URA3. Selectable markers for use in a filamentous fungal host cell include, but are not limited to, amdS (acetamidase), argB (ornithine carbamoyltransferase), bar (phosphinothricin acetyltransferase), hygB (hygromycin phosphotransferase), niaD (nitrate reductase), pyrG (orotidine-5'-phosphate decarboxylase), sC (sulfate adenyltransferase), trpC (anthranilate synthase), as well as equivalents thereof.

Preferred for use in an *Aspergillus* cell are the amdS and pyrG genes of *Aspergillus nidulans* or *Aspergillus oryzae* and the bar gene of *Streptomyces hygroscopicus*.

The vectors of the present invention preferably contain an element(s) that permits stable integration of the vector into the host cell's genome or autonomous replication of the vector in the cell independent of the genome.

For integration into the host cell genome, the vector may rely on the nucleotide sequence encoding the polypeptide or any other element of the vector for stable integration of the vector into the genome by homologous or nonhomologous recombination. Alternatively, the vector may contain additional nucleotide sequences for directing integration by homologous recombination into the genome of the host cell. The additional nucleotide sequences enable the vector to be integrated into the host cell genome at a precise location(s) in the chromosome(s). To increase the likelihood of integration at a precise location, the integrational elements should preferably contain a sufficient number of nucleotides, such as 100 to 1,500 base pairs, preferably 400 to 1,500 base pairs, and most preferably 800 to 1,500 base pairs, which are highly homologous with the corresponding target sequence to enhance the probability of homologous recombination. The integrational elements may be any sequence that is homologous with the target sequence in the genome of the host cell. Furthermore, the integrational elements may be non-encoding or encoding nucleotide sequences. On the other hand, the vector may be integrated into the genome of the host cell by non-homologous recombination.

For autonomous replication, the vector may further comprise an origin of replication enabling the vector to replicate autonomously in the host cell in question. Examples of origins of replication for use in a yeast host cell are the 2 micron origin of replication, ARS1, ARS4, the combination of ARS1 and CEN3, and the combination of ARS4 and CEN6. The origin of replication may be one having a mutation which makes its functioning temperature-sensitive in the host cell (see, e.g., Ehrlich, 1978, *Proceedings of the National Academy of Sciences USA* 75: 1433).

More than one copy of a nucleotide sequence of the present invention may be inserted into the host cell to increase production of the gene product. An increase in the copy number of the nucleotide sequence can be obtained by integrating at least one additional copy of the sequence into the host cell genome or by including an amplifiable selectable marker gene with the nucleotide sequence where cells containing amplified copies of the selectable marker gene, and thereby additional copies of the nucleotide sequence, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant a host cell comprising the nucleic acid construct of the invention, which are advantageously used in the recombinant production of the polypeptides. A vector comprising a nucleotide sequence of the present invention is introduced into a host cell so that the vector is maintained as a chromosomal integrant or as a self-replicating extra-chromosomal vector as described earlier.

The host cell may be a eukaryote, such as a mammalian, insect, plant, or fungal cell. For cloning purposes the host cell may be a bacterial cell as well, e.g. an *E. coli* cell.

In a preferred embodiment, the host cell is a fungal cell. "Fungi" as used herein includes the phyla Ascomycota, Basidiomycota, Chytridiomycota, and Zygomycota (as defined by Hawksworth et al., In, *Ainsworth and Bisby's Dictionary of The Fungi*, 8th edition, 1995, CAB International, University Press, Cambridge, UK) as well as the Oomycota (as cited in Hawksworth et al., 1995, supra, page 171) and all mitosporic fungi (Hawksworth et al., 1995, supra).

In a more preferred embodiment, the fungal host cell is a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in *Biology and Activities of Yeast* (Skinner, F. A., Passmore, S. M., and Davenport, R. R., eds, *Soc. App. Bacterol. Symposium Series* No. 9, 1980).

In an even more preferred embodiment, the yeast host cell is a *Candida, Hansenula, Kluyveromyces, Pichia, Saccharomyces, Schizosaccharomyces*, or *Yarrowia* cell.

In a most preferred embodiment, the yeast host cell is a *Saccharomyces carlsbergensis, Saccharomyces cerevisiae, Saccharomyces diastaticus, Saccharomyces douglasii, Saccharomyces kluyveri, Saccharomyces norbensis* or *Saccharomyces oviformis* cell. In another most preferred embodiment, the yeast host cell is a *Kluyveromyces lactis* cell. In another most preferred embodiment, the yeast host cell is a *Yarrowia lipolytica* cell.

In another more preferred embodiment, the fungal host cell is a filamentous fungal cell. "Filamentous fungi" include all filamentous forms of the subdivision Eumycota and Oomycota (as defined by Hawksworth et al., 1995, supra). The filamentous fungi are characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

In an even more preferred embodiment, the filamentous fungal host cell is a cell of a species of, but not limited to, *Acremonium, Aspergillus, Fusarium, Humicola, Mucor, Myceliophthora, Neurospora, Penicillium, Thielavia, Tolypocladium*, or *Trichoderma*.

In a most preferred embodiment, the filamentous fungal host cell is an *Aspergillus awamori, Aspergillus foetidus, Aspergillus japonicus, Aspergillus nidulans, Aspergillus niger* or *Aspergillus oryzae* cell. In another most preferred embodiment, the filamentous fungal host cell is a *Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides*, or *Fusarium venenatum* cell. In an even most preferred embodiment, the filamentous fungal parent cell is a *Fusarium venenatum* (Nirenberg sp. nov.) cell. In another most preferred embodiment, the filamentous fungal host cell is a *Humicola insolens, Humicola lanuginosa, Mucor miehei, Myceliophthora thermophila, Neurospora crassa, Penicillium purpurogenum, Thielavia terrestris, Trichoderma harzianum, Trichoderma koningii, Trichoderma longibrachiatum, Trichoderma reesei*, or *Trichoderma viride* cell.

Fungal cells may be transformed by a process involving protoplast formation, transformation of the protoplasts, and regeneration of the cell wall in a manner known per se. Suitable procedures for transformation of *Aspergillus* host cells are described in EP 238 023 and Yelton et al., 1984, *Proceedings of the National Academy of Sciences USA* 81: 1470-1474. Suitable methods for transforming *Fusarium* species are described by Malardier et al., 1989, *Gene* 78: 147-156 and WO 96/00787. Yeast may be transformed using the procedures described by Becker and Guarente, In Abelson, J. N. and Simon, M. I., editors, *Guide to Yeast Genetics and Molecular Biology, Methods in Enzymology*, Volume 194, pp 182-187, Academic Press, Inc., New York; Ito et al., 1983, *Journal of Bacteriology* 153: 163; and Hinnen et al., 1978, *Proceedings of the National Academy of Sciences USA* 75: 1920.

Methods of Production

The present invention also relates to methods for producing a polypeptide of the present invention comprising (a) cultivating a strain, which in its wild-type form is capable of producing the polypeptide; and (b) recovering the polypeptide. Preferably, the strain is of the genus *Aspergillus*, and more preferably *Aspergillus oryzae*.

The present invention also relates to methods for producing a polypeptide of the present invention comprising (a) cultivating a host cell under conditions conducive for production of the polypeptide; and (b) recovering the polypeptide.

In the production methods of the present invention, the cells are cultivated in a nutrient medium suitable for production of the polypeptide using methods known in the art. For example, the cell may be cultivated by shake flask cultivation, small-scale or large-scale fermentation (including continuous, batch, fed-batch, or solid state fermentations) in laboratory or industrial fermentors performed in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

The polypeptides may be detected using methods known in the art that are specific for the polypeptides. These detection methods may include use of specific antibodies, formation of an enzyme product, or disappearance of an enzyme substrate. For example, an enzyme assay may be used to determine the activity of the polypeptide as described herein.

The resulting polypeptide may be recovered by methods known in the art. For example, the polypeptide may be recovered from the nutrient medium by conventional procedures including, but not limited to, centrifugation, filtration, extraction, spray-drying, evaporation, or precipitation.

The polypeptides of the present invention may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, J.-C. Janson and Lars Ryden, editors, VCH Publishers, New York, 1989).

Compositions

In a still further aspect, the present invention relates to compositions comprising a polypeptide of the present invention.

The composition may comprise a polypeptide of the invention as the major enzymatic component, e.g., a mono-component composition. Alternatively, the composition may comprise multiple enzymatic activities, such as an aminopeptidase, amylase, carbohydrase, carboxypeptidase, catalase, cellulase, chitinase, cutinase, cyclodextrin glycosyltransferase, deoxyribonuclease, esterase, alpha-galactosidase, beta-galactosidase, glucoamylase, alpha-glucosidase, beta-glucosidase, haloperoxidase, invertase, laccase, lipase, mannosidase, oxidase, pectinolytic enzyme, peptidoglutaminase, peroxidase, phytase, polyphenoloxidase, proteolytic enzyme, ribonuclease, transglutaminase, or xylanase.

The compositions may be prepared in accordance with methods known in the art and may be in the form of a liquid or a dry composition. For instance, the polypeptide composition may be in the form of a granulate or a microgranulate. The polypeptide to be included in the composition may be stabilized in accordance with methods known in the art.

Examples are given below of preferred uses of the polypeptide compositions of the invention. The dosage of the polypeptide composition of the invention and other conditions under which the composition is used may be determined on the basis of methods known in the art.

Biofilms

Microorganisms growing in biofilms are less susceptible to all types of antimicrobial agents than the same microorganisms when grown in conventional suspension cultures.

It is well known that starved bacteria can be much less susceptible to a variety of antimicrobial challenges. For example, a number of classical antibiotics such as penicillin, perform poorly in slow or non dividing bacteria. Because lysozyme attacks and destroys the peptidoglycan layer regardless of the growth state of the bacteria, it remains effective.

Biofilm Control; Example Dental Water Lines:

Biofilm buildup within a dental water line can contain biofilms consisting of, *Pseudomonas aeroginosa, Proteus mirabilis, Leigonella* sp. to name but a few. There is also the possibility of colonisation of species generally found within the oral cavity as a result of the failure of anti retraction valves within the system. The risk of cross infection becomes even more of a potential risk of course when immuno—compromised patients are involved and in this day and age the numbers of patients within this category continues to steadily increase. The need exists for effective control of bacterial biofilm accumulation in dental water lines. A review of biofilms can be found: Watnick P and Kolter R. (2000) Biofilm, city of microbes. J Bacteriol.; 182(10):2675-9.

A typical example of a commercial throat lozenge product is Lysopaine produced by: BOEHRINGER INGELHEIM FRANCE Active Ingredients:
BACITRACIN 200 U.I.
(to 65 iu/mg)
PAPAIN 2 mg
to 30 NK/mg
LYSOZYME CHLORHYDRATE 5 mg
to 26000 U FIP/mg: units determined by measuring OD kinetics of lysis of bacteria suspended in buffer. The unit determination was measured by lysis induced change in turbididy of a bacterial culture suspended in buffer.

Non Active Ingredients:
SACCHARIN excipient
MAGNESIUM STEARATE excipient
Menthol aromatisant
SORBITOL excipient For local treatment of point infections limited to the buccal membranes of the oropharynx. Caution, if clinical indications of a general bacterial infection are evident, antibiotic therapy is advised.

Toothpaste:

Lysozyme can be used alone or in combination with other enzymes or even antimicrobial peptides. Examples of other enzymes: Glucose oxidase, lactoperoxidase A typical toothpaste composition including lysozyme is "Biotene: by Laclede, Inc.

2030 East University Drive, Rancho Domiguez, Calif. 90220, USA

Ingredients
Active Ingredients
Contains: Lactoperoxidase (100gm)
Inactive Ingredients
Glucose Oxidase, Lysozyme, Sodium Monofluorophosphate, Sorbitol, Glycerin, Calcium Pyrophosphate, Hydrated Silica, Zylitol, Cellulose Gum, Flavor, Sodium Benzoate, Beta-d-glucose, Potassium Thiocyanate Detergent Composition The lysozyme of the invention may be added to and thus become a component of a detergent composition, particularly in a liquid detergent having a pH of 7 or lower.

The detergent composition of the invention may for example be formulated as a hand or machine laundry detergent composition including a laundry additive composition suitable for pre-treatment of stained fabrics and a rinse added fabric softener composition, or be formulated as a detergent composition for use in general household hard surface cleaning operations, or be formulated for hand or machine dishwashing operations.

In a specific aspect, the invention provides a detergent additive comprising the lysozyme of the invention. The detergent additive as well as the detergent composition may comprise one or more other enzymes such as a protease, a lipase, a cutinase, an amylase, a carbohydrase, a cellulase, a pectinase, a mannanase, an arabinase, a galactanase, a xylanase, an oxidase, e.g., a laccase, and/or a peroxidase.

In general the properties of the chosen enzyme(s) should be compatible with the selected detergent, (i.e. pH-optimum, compatibility with other enzymatic and non-enzymatic ingredients, etc.), and the enzyme(s) should be present in effective amounts.

DNA Recombination (Shuffling)

The nucleotide sequence of SEQ ID NO:1 may be used in a DNA recombination (or shuffling) process. The new polynucleotide sequences obtained in such a process may encode new polypeptides having lysozyme activity with improved properties, such as improved stability (storage stability, thermo stability), improved specific activity, improved pH-optimum, and/or improved tolerance towards specific compounds.

Shuffling between two or more homologous input polynucleotides (starting-point polynucleotides) involves fragmenting the polynucleotides and recombining the fragments, to obtain output polynucleotides (i.e. polynucleotides that have been subjected to a shuffling cycle) wherein a number of nucleotide fragments are exchanged in comparison to the input polynucleotides.

DNA recombination or shuffling may be a (partially) random process in which a library of chimeric genes is generated from two or more starting genes. A number of known formats can be used to carry out this shuffling or recombination process.

The process may involve random fragmentation of parental DNA followed by reassembly by PCR to new full-length genes, e.g. as presented in U.S. Pat. No. 5,605,793, U.S. Pat. No. 5,811,238, U.S. Pat. No. 5,830,721, U.S. Pat. No. 6,117, 679. In-vitro recombination of genes may be carried out, e.g. as described in U.S. Pat. No. 6,159,687, WO98/41623, U.S. Pat. No. 6,159,688, U.S. Pat. No. 5,965,408, U.S. Pat. No.

6,153,510. The recombination process may take place in vivo in a living cell, e.g. as described in WO 97/07205 and WO 98/28416.

The parental DNA may be fragmented by DNA'se I treatment or by restriction endonuclease digests as described by Kikuchi et al (2000a, Gene 236:159-167). Shuffling of two parents may be done by shuffling single stranded parental DNA of the two parents as described in Kikuchi et al (2000b, Gene 243:133-137).

A particular method of shuffling is to follow the methods described in Crameri et al, 1998, Nature, 391: 288-291 and Ness et al. Nature Biotechnology 17: 893-896. Another format would be the methods described in U.S. Pat. No. 6,159, 687: Examples 1 and 2.

The present invention is further described by the following examples which should not be construed as limiting the scope of the invention.

EXAMPLES

Example 1

The Cloning of a GH 25 Lysozyme From *Trametes Cinnabarina*

*Trametes cinnabarina* (=*Pycnoporus cinnabarinus*) CBS114004, *Polyporaceae, Polyporales, Agricomycetidae, Basidiomycetes, Basidiomycota*. The strain was isolated from dead branches of *Castannna mollissima*, collected from Huairou county, Beijing, China, by Wen Ping Wu, September 2002. The strain was definitively identified as *Trametes cinnabarina* (*Pycnoporus cinnabarinus*) Oct. 11, 2002, by Wenping Wu. The fungal strain was deposited on 17 November at Centraal Bureau voor Schimmelcultures, Uppsalalaan 8, P.O. Box 85167, 3508 AD Utrecht, The Netherlands, under the accession number CBS114004.

Fermentation and Enzyme Fingerprinting:

The fungal strain CBS114004 was fermented in two medias; FG4 and MEX-1 media at 25 degrees C., 160 rpm for 6 days. Culture fluids were tested for enzyme activity assay by standard enzyme fingerprinting assay: (Enzyme fingerprinting of culture fluids.

Enzyme fingerprinting: An enzyme activity profile was obtained by assaying the culture broth on a wide spectrum of enzyme assays. 96 wells microtitre (MT) plates are prepared with substrates and stored at +10° C. until use. Two different pH varieties are prepared: pH3 and pH7. Following substrates are used: 0.05% AZCL (Mazurine dyed and cross-linked substrates, Megazyme)—Amylose, Arabinan, Beta Glucan (Barley), Casein, Collagen, Curdlan, Dextran, Galactan (potato), Galactomannan (Carob), He-Cellulose, Pullulan, Xylan (oat), and Xyloglucan (AZCL-casein can not be used at pH3, and is therefore left out from these plates). Preparation of substrates: pH3 plates: 0.1 g of each AZCL substrate is dissolved in 100 ml 0.2M Succinic acid pH3+10 ul TritonX-100 (0.01%), to give a final concentration of 0.1% AZCL. pH7 plates: 0.1 g of each AZCL substrate is dissolved in 50 ml sterile H20 plus 10 ul TritonX-100 (0.01%). 50 ml 0.4M MOPS pH 7 is added to each 50 ml AZCL substrate, to give a final volume of 100 ml and a final concentration of 0.2M buffer, 0.1% AZCL. Laccase and lipase activity assays are included and prepared as follows:

Laccase: 35 ml 0.08 mg/ml Chicago Sky Blue in 0.2 M phosphate/borate-buffer, pH 9 Lipase: A polyvinyl alcohol (PVA)/soybean oil emulsion is prepared by mixing a 2% PVA solution with soybean oil 3:1. Emulsify the oil using ULTRA-TURRAX and mix 12 ml of the emulation with 500 ml 0.2M sodium-acetate buffer including 10 mM CaCl2 pH 5.5 and 5 ml 0.2% Crystal Violet solution. The MT plates are prepared using a Multidrop S20 Stacker, Titertek Instruments, Inc., Alabama, and US. Sterilin 96-wells MT plates are used. 200 µl of each AZCL-substrate and of the lipase substrate and 150 µl of the laccase substrate are dispensed into MT wells and 30-50 µl culture broth are added to each substrate and incubated over night at 26 degree Celsius. Result scores are made in the assays as follows: 0: no activity, 1: weak activity, 2: strong activity. The mycelium was harvested at 6 days, when the sample showed many different enzyme activities and stored under −80 degrees until used for cDNA library construction.

Total RNA Isolation:

A Modified Fenozol total RNA extraction method (Active Motif, Inc) was used.

Materials:

Fenozol from Active motif Cat. nr. 2100
RNAse free eppendorf tubes, tips
RNase free Chloroform
RNase free isopropanol
RNase free 96% and 70% EtOH
RNase free 3 M NAOAc pH 5,2
Phenol-chloroform-mix
CIA(Chloroform:isoamylalcohol, 24:1)
The following material was baked at 250° C. for 12 hours:
quartz sand
metal spoons
morter and pestle
150 ml glass beakers 20 ml Fenozol in a 150 ml baked glass beaker. Preserved mycelia (−80° C.) was ground with baked quartz sand in a pre chilled mortar and pestle under liquid nitrogen. The ground material was transferred with a spoon to the beaker and mixed rapidly to dissolve the frozen material into a thick suspension. The beaker containing the material was transferred to a 50 C. water bath for 15 minutes. The material was then transferred to an Oakridge tube and 5 ml "RNase free" chloroform was added. The sample was then vortexed vigorously and then allowed to stand at room temperature for 10 minutes. The tubes were centrifuged at 12,000 g, room temperature for 20 minutes and then the top phase was transferred to a new Oakridge tube. An equal volume of phenol-chloroform mixture was added and the sample was then vortexed vigorously and centrifuged under the same conditions. The sample (top phase was transferred to a new tube and add an equal volume of CIA was added and the vortex and centrifugation step repeated but with only a 10 minute centrifugation. The aqueous phase was transferred to a new tube and 6.25 ml isopropanol was added, mixed and the material was then incubated at room temperature for 15 minutes. The tubes were then centrifuged at 12,000 g for 30 minutes, 4° C. The supernatant was carefully removed and 18 ml of 70% ethanol was carefully added. The tubes were centrifuged for 5 minutes, 4° C. at 12,000 g and then the supernatant was removed and the pellet air dried. The RNA pellet was re-suspended in 500 µl DEPC (Dimethylpyrocarbonate)treated water. Heating at 65° C. for 10 minutes to aided in re-suspension. The total RNA was stored at −80° C. until further use.

PolyA Enriched RNA Production:

The mTrap Midi mRNA isolation kit from Active Motif was used (Active Motif, Europe). The polyA enriched RNA was purified according to the manufacturer's instruction with the following modification: the total RNA suspension isolated as described above, was used as starting material. 15 ml of the lysis buffer, without protease, was added to approximately 20 µg of total RNA. The mRNA fractions were eluted by column chromatography as described in the protocol and the pools representing 0.5 kb and larger were chosen for cDNA synthesis.

Creation of a cDNA Library:

The Smart cDNA construction kit (K1051-1, BD Biosciences) was used with the following modifications: After the second strand cDNA synthesis step, the material was purified by GFX spin chromatography according to the manufacturer's instructions (AP Pharma) and the material eluted in 85 µl of deionised $H_2O$. After SfiI digestion, the treated cDNA was size fractionated by EtBr Gel purification according to the method below:

1) Prepare a 0.8% SeaPlaque LMP agarose gel in 1×TBE (in autoclaved LiChroSolv/HPLC $H_2O$)+ETBr in gel and buffer. Add loading buffer to 100 uls of the SfiI digestion from step D and run at 15 V in a clean electrophoresis cell overnight with DNA markers flanking the sample.

2) On a UV box and long wave UV (360 nm), visualize the cDNA and DNA markers. With a scalpel remove all of the gel below 500 bp and remove the top of the sample wells. Slide the remaining gel down on the cell and pour a 1.5% Seaplaque EtBr agarose gel above the sample wells.

3) Reverse the polarity of the electrophoresis unit and run the DNA a short distance into the 1.5% agarose gel.

4) Perform standard gel excision under long wave UV and GFX purification of the gel fragment.

The sample was ligated into the vector pMHas5 in a standard ligation reaction using T4 DNA ligase (New England Biolabs, Inc), according to the manufacturer's instructions. The pMhas5 plasmid and use of a fungal cDNA library produced in the plasmid is described in patent application WO2003044049. The same methodology was used to identify the *Trametes* GH25 lysozyme from the SigA4 transposon treated library as described in WO2003044049. Sequence, SEQ ID 1, was identified in the original BLAST hit as having strong similarity to both the GENESEQP:AAW85696 *Streptomyces rutgersensis* glycosyl hydrolase GH 25 and the fungal sequence SWISSPROT:P00721 *Chalaropsis* sp. GH 25 peptide sequence and a number of other less well annotated *Streptomyces* open reading frames from genome sequencing products (*Streptomyces coelicolor*, Q9FBR0) (See homology matrix Table 1). Based on this information, it was decided to express the *Trametes* GH 25 candidate in *Aspergillus oryzae*.

TABLE 1

Homology table of top scoring GH25 hydrolases found in public databanks

|  | Chalaropsis | NP001276 | AAW85696 | Q9FBR0 |
|---|---|---|---|---|
| Chalaropsis | 100 | 60 | 32 | 40 |
| NP001276 |  | 100 | 40 | 53 |
| AAW85696 |  |  | 100 | 45 |
| Q9FBR0 |  |  |  | 100 |

AAW85696, *Streptomyces rutgersensis*;
Q9FBR0, *Streptomyces coelicolor*;
NP001276 the GH25 of the invention;
Chalaropsis (SWISSPROT:P00721)

Example 2

Expression of GH25 Enzyme From *Trametes* of the Invention:

The Sequence ID no 1 was used to design custom oligo nucleotide primers for use in a PCR reaction to generate an insert encoding the enzyme of the invention, flanked by restriction enzyme sites facilitating cloning into an expression vector.

```
Primers:
Primer 1 (Seq ID No 3), NP1276 EcoRI
5'-GCGGAATTCAACATGAAGCTCTCTACCACAGCTC-3'

Primer 2, (Seq ID No 4), NP1276 NotI
5'-ATATGCGGCCGCAAAGTTACGAAGCTGCGAATTGTC-3'
```

The underlined portions are additional DNA sequences added to the primers to incorporate restriction enzyme sites used in cloning.

The GH25 lysozyme encoding sequence was amplified from the above cDNA library (see Example 1 above) in the following manner: 1 microliter of cDNA (approximately 10 nanogram of DNA) was used as template in a PCR reaction with the two primers NP1276EcoRI and NP1276NotI.

```
NP1276 EcoRI:                          (SEQ ID NO: 3)
5'-GCGGAATTCAACATGAAGCTCTCTACCACAGCTC-3'

NP1276 NotI:                           (SEQ ID NO: 4)
5'-ATATGCGGCCGCAAAGTTACGAAGCTGCGAATTGTC-3'
```

10 pmole of each primer were used in a 100 microliter reaction volume. The ProofStart polymerase (Qiagen GMBH) was used in conditions recommended by the supplier. After an initial 10 minute heat treatment at 94 degrees C. the conditions were as follows: Denaturation temperature; 94 degrees Celsius-30 seconds, annealing temperature; 55 degrees Celsius-30 seconds, and extension at 72 degrees Celsius for 1 minute. A total of 35 cycles were run.

Aliquots of the PCR reaction were separated on a 1% agarose gel. A single distinct band at the predicted 820 base pairs was seen. The fragment was isolated from the gel by GFX spin chromatography (AB Pharma) and digested with EcoRI and NotI which cut in the overhangs introduced by the PCR primers. The digested fragments were isolated and cloned into pXYG1051, an *Aspergillus* expression plasmid based on the plasmid pMStr46 (see the examples of international patent application WO2003070956). Specifically, the AMA autonomous replication region was removed by HindIII digestion and relegation resulting in an integrative vector. After standard ligation, transformation into DH10B *E. coli*, colonies that grew under ampicillin selection on LB plates were identified. 10 colonies were chosen in order to prepare plasmid DNA. The resulting plasmid DNA was sequenced using the vector primers of pXYG1051 revealed in patent application WO2003070956. One of the clones that was without PCR errors (NP001276-4) was chosen for a Qiagen midi scale plasmid prep (Qiagen GMBH).

The chosen clone (NP001276-4) was used for expression of the enzyme in *Aspergillus* (see below) and the EcoRI and NotI insert comprising the gene of the invention was used for subcloning the fragment into a standard bacterial vector, pBlueScript KS+ (Stratagene Inc.), and transformation into the *E. coli* strain DH10B (from Clontech). This strain was deposited 8 Dec. 2003 at Deutsche Sammlung von Mikroorganismen und Zellkulturen GmbH, Mascheroder Weg 1b, D-38124 Braunschweig, Germany, under the accession number DSM 16084.

Expression of Clone NP001276 in *Aspergillus*:

The cDNA clone, NP001276-4, was transformed into *Aspergillus oryzae* strain Jal355 (disclosed in international patent application WO2003070956). 30 transformants were re-isolated twice under selective and non-inducing conditions on Cove nitrate minimal plates with sucrose as the carbon source. To test expression of NP1276, transformants were grown for 4 days at 30 degrees Celsius in tubes with 10 ml YPM (2% peptone, 1% yeast extract, 2% maltose). Supematants were run on NuPage 10% Bis-Tris SDS gels (Invitrogen) as recommended by the manufacturer. The *Aspergillus* strains grew well even when induced for the expression of Plectasin with maltose. A distinct band of the size expected for GH 25 lysozyme (23 kDa) was seen in most transformants, whereas this band was not seen in the untransformed host strain *A. oryzae* BECh2. A single, strongly expressing *Aspergillus* transformant (EXP00787) was chosen for continued study. A large scale shake flask experiment was performed with 20×1000 ml Erlingmeyer shake flasks with three baffles. Each flask contained 100 mls FG4P media (FG4P: 3% Soybean meal (SFK 102-2458), 1.5% Maltodextrin (Roquette), 0.5% Pep-tone bacto (Difco 0118), 1.5% $KH_2PO_4$ (Merck 4873), 0.2 mls/liter Pluronic PE 6100 (BASF)). Conditions used: 30 Degrees C., 150 RPM, 3 days growth. The culture fluid was harvested by filtration though two layers of miracloth and frozen until used.

Example 3

Purification of GH25 Enzyme of the Invention:
Description of Purification:
1.7 l of fermentation broth was germ filtrated and purified on a SP-sepharose column using 50 mM NaAc pH 5/50 mM NaAc, 1M NaCl pH 5. The pooled fractions were concentrated on Amicon cell (Millipore) with a cut off 10 kDa. The N-terminal amino acid sequence (EKRANPKGID) confirmed that the purified protein was mature GH25 enzyme.

Example 4

Detection of Lysozyme Activity by a Cell Wall Assay.
Lyophilized cells of *Micrococcus lysodeikticus* (Sigma) was used as substrate The substrate was suspended in a Britton&Robinson buffer (0.08 M phosphoric acid, 0.08 M boric acid and 0.08 M acetic acid; pH adjusted to 2-12 with 1 M NaOH) at the appropriate pH to a final concentration of 0.3 mg/ml. To each well in a 96 well microtiter plate was added 100 μl substrate suspension and 30 μl enzyme solution at a concentration of approximately 1 mg/ml. Changes in turbidity was measured in a microplate reader at 450 nm for 5 minutes after addition of the enzyme. The slope of the curve was calculated and used as a relative measure of enzyme activity.

Temperature curve: The purified enzyme was incubated at 40°, 50°, 60° and 70° C. for 15 min. Samples were cooled to RT and the relative residual activity at pH 5 was measured in the above mentioned assay. The enzyme was stable up to 50° C.

TABLE 2

| Temperature, ° C. | Relative residual activity, % |
|---|---|
| 40 | 100 |
| 50 | 98 |
| 60 | 64 |
| 70 | 28 | pH curve: Substrate suspensions at pH 4, 5, 6, 7 and 8 were prepared, and relative activity of the enzyme was measured as described above. The enzyme has pH optimum at pH 5.

TABLE 3

| pH | Relative activity, % |
|---|---|
| 4 | 35 |
| 5 | 100 |
| 6 | 41 |
| 7 | 20 |
| 8 | 15 |

Deposit of Biological Material

The following biological material has been deposited under the terms of the Budapest Treaty with the Deutsche Sammlung von Mikroorganismen und Zellkulturen GmbH, Mascheroder Weg 1 B, D-38124 Braunschweig, Germany, and given the following accession number:

| Deposit | Accession Number | Date of Deposit |
|---|---|---|
| *E. coli* DH10B | DSM 16084 | Dec. 5, 2003 |

The following biological material has been deposited under the terms of the Budapest Treaty with the Centraal Bureau voor Schimmelcultures, Uppsalalaan 8, P.O. Box 85167, 3508 AD Utrecht, The Netherlands, and given the following accession number:

| Deposit | Accession Number | Date of Deposit |
|---|---|---|
| *Trametes cinnabarina* | CBS 114004 | Nov. 17, 2003 |

The invention claimed is:

1. An isolated polypeptide having lysozyme activity and belonging to the GH25 family selected from the group consisting of:
   (a) a polypeptide comprising an amino acid sequence, which has at least 90% identity with the sequence of amino acids 1 to 233 of SEQ ID NO: 2; and
   (b) a fragment of the sequence of amino acids 1 to 233 of SEQ ID NO: 2 that has lysozyme activity.

2. The polypeptide of claim 1, comprising an amino acid sequence, which has at least 95% identity with the sequence of amino acids 1 to 233 of SEQ ID NO: 2.

3. The polypeptide of claim 1, comprising an amino acid sequence, which has at least 96% identity with the sequence of amino acids 1 to 233 of SEQ ID NO: 2.

4. The polypeptide of claim 1, comprising an amino acid sequence, which has at least 97% identity with the sequence of amino acids 1 to 233 of SEQ ID NO: 2.

5. The polypeptide of claim 1, comprising an amino acid sequence, which has at least 98% identity with the sequence of amino acids 1 to 233 of SEQ ID NO: 2.

6. The polypeptide of claim 1, comprising an amino acid sequence, which has at least 99% identity with the sequence of amino acids 1 to 233 of SEQ ID NO: 2.

7. The polypeptide of claim 1, which comprises the sequence of amino acids 1 to 233 of SEQ ID NO: 2.

8. The polypeptide of claim 1, which consists of the sequence of amino acids 1 to 233 of SEQ ID NO: 2.

9. The polypeptide of claim 1, which is a fragment of the sequence of amino acids 1 to 233 of SEQ ID NO: 2 that has lysozyme activity.

10. A composition comprising the polypeptide of claim 1 and a surfactant.

11. An animal feed comprising the polypeptide of claim 1.

12. A method for inhibiting biofilm formation, comprising applying the polypeptide of claim 1.

* * * * *

UNITED STATES PATENT AND TRADEMARK OFFICE
CERTIFICATE OF CORRECTION

PATENT NO. : 7,635,470 B2 Page 1 of 1
APPLICATION NO. : 10/586026
DATED : December 22, 2009
INVENTOR(S) : Wu et al.

It is certified that error appears in the above-identified patent and that said Letters Patent is hereby corrected as shown below:

On the title page, item (22), delete the PCT Filing date of "February 16, 2006" and insert
-- February 16, 2005 --.

On the title page under the heading "OTHER PUBLICATIONS", insert
-- EMBL-EBI, XP-002328312 (1990) -- at the bottom of the list.

Signed and Sealed this

Sixteenth Day of March, 2010

David J. Kappos
*Director of the United States Patent and Trademark Office*

UNITED STATES PATENT AND TRADEMARK OFFICE
CERTIFICATE OF CORRECTION

PATENT NO. : 7,635,470 B2  Page 1 of 1
APPLICATION NO. : 10/586026
DATED : December 22, 2009
INVENTOR(S) : Wu et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 478 days.

Signed and Sealed this

Twenty-first Day of December, 2010

David J. Kappos
*Director of the United States Patent and Trademark Office*

SEQUENCE LISTING

```
<160> NUMBER OF SEQ ID NOS: 4

<210> SEQ ID NO 1
<211> LENGTH: 945
<212> TYPE: DNA
<213> ORGANISM: Trametes cinnabarina

<400> SEQUENCE: 1
ggccattacg gccggggtg cacagacgtc ggtgtccgag cacatcctat ctcactcaag      60
cttagaccac cttgggctac gacatgaagc tctctaccac agctctgctt gctattgcgg    120
```

-continued

```
tggcagtggc ctctgcttct cccactcccg agaagcgtgc caacccccaag ggcattgacg     180 tctcggctta ccaacccaac atcaactgga gcaccgtcaa agccaacggg atctcgttcg     240
catatatcaa ggcaaccgag ggtaccacgt ataccaaccc agacttctcg agccagtata     300
caggcgcgac taatgctgga ctcattcggg gcggctacca cttcgcccat cccgactcct     360
cttcaggcgc gactcaagcc aagtacttcc tggcccacgg aggtggatgg acaagcgacg     420
gaatcacact tccaggcgct ctcgacatcg agtataaccc tagcggggcg gagtgttatg     480
gcttaagcgc gtcggcgatg gtttcgtgga tcaaagactt ctccaatacc taccactcgt     540
cgaccggagt ttaccctgtt atttacacca ccacggactg gacgacgaca tgcacgggca     600
acagtgccgc gtttgcttcg acgaaccctc tatggattgc ccgctatgca tcaagcatcg     660
gcaccctgcc cgcaggttgg agttatacaa cgttctggca atatgctgac tcgggcccga     720
accctggtga ccaggatgag ttcaatggct cgatggcagg actgaagcag cttgcgctcg     780
ggtgaagtgg gatgtgaggt cgccggagaa gaagcagagt ccaccggcag cagtatccgt     840
cgtgtacatc atggtgtcat accatccgaa gacgatactc gagtcgtacg gacaattcgc     900
agcttcgtaa ctttgaaaaa aaaaaaaaaa aaaaaaaaaa aaaaa                     945
```

<210> SEQ ID NO 2
<211> LENGTH: 233
<212> TYPE: PRT
<213> ORGANISM: Trametes cinnabarina

<400> SEQUENCE: 2

```
Met Lys Leu Ser Thr Thr Ala Leu Leu Ala Ile Ala Val Ala Val Ala
1               5                   10                  15

Ser Ala Ser Pro Thr Pro Glu Lys Arg Ala Asn Pro Lys Gly Ile Asp
            20                  25                  30

Val Ser Ala Tyr Gln Pro Asn Ile Asn Trp Ser Thr Val Lys Ala Asn
        35                  40                  45

Gly Ile Ser Phe Ala Tyr Ile Lys Ala Thr Glu Gly Thr Thr Tyr Thr
    50                  55                  60

Asn Pro Asp Phe Ser Ser Gln Tyr Thr Gly Ala Thr Asn Ala Gly Leu
65                  70                  75                  80

Ile Arg Gly Gly Tyr His Phe Ala His Pro Asp Ser Ser Gly Ala
                85                  90                  95

Thr Gln Ala Lys Tyr Phe Leu Ala His Gly Gly Trp Thr Ser Asp
            100                 105                 110

Gly Ile Thr Leu Pro Gly Ala Leu Asp Ile Glu Tyr Asn Pro Ser Gly
        115                 120                 125

Ala Glu Cys Tyr Gly Leu Ser Ala Ser Ala Met Val Ser Trp Ile Lys
    130                 135                 140

Asp Phe Ser Asn Thr Tyr His Ser Ser Thr Gly Val Tyr Pro Val Ile
145                 150                 155                 160

Tyr Thr Thr Thr Asp Trp Trp Thr Thr Cys Thr Gly Asn Ser Ala Ala
                165                 170                 175

Phe Ala Ser Thr Asn Pro Leu Trp Ile Ala Arg Tyr Ala Ser Ser Ile
            180                 185                 190

Gly Thr Leu Pro Ala Gly Trp Ser Tyr Thr Thr Phe Trp Gln Tyr Ala
        195                 200                 205

Asp Ser Gly Pro Asn Pro Gly Asp Gln Asp Glu Phe Asn Gly Ser Met
    210                 215                 220

Ala Gly Leu Lys Gln Leu Ala Leu Gly
```

```
225                 230

<210> SEQ ID NO 3
<211> LENGTH: 34
<212> TYPE: DNA
<213> ORGANISM: Artificial
<220> FEATURE:
<223> OTHER INFORMATION: Upstream PCR primer for Seq ID no 1 having an
      EcoR1 site added

<400> SEQUENCE: 3
gcggaattca acatgaagct ctctaccaca gctc                               34

<210> SEQ ID NO 4
<211> LENGTH: 36
<212> TYPE: DNA
<213> ORGANISM: Artificial
<220> FEATURE:
<223> OTHER INFORMATION: Downsteam PCR primer for Seq ID no 1 having a
      Not1 site added

<400> SEQUENCE: 4
atatgcggcc gcaaagttac gaagctgcga attgtc                             36
```